United States Patent
Palese

(10) Patent No.: US 10,327,753 B2
(45) Date of Patent: Jun. 25, 2019

(54) KNOTLESS SUTURE ANCHOR AND METHOD OF USING SAME

(71) Applicant: Biomet Sports Medicine, LLC, Warsaw, IN (US)

(72) Inventor: Christopher Palese, South Whitley, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 488 days.

(21) Appl. No.: 14/876,204

(22) Filed: Oct. 6, 2015

(65) Prior Publication Data

US 2016/0022260 A1 Jan. 28, 2016

Related U.S. Application Data

(63) Continuation of application No. 13/791,072, filed on Mar. 8, 2013, now Pat. No. 9,192,371.

(51) Int. Cl.
*A61B 17/04* (2006.01)
*A61B 17/34* (2006.01)

(52) U.S. Cl.
CPC .. *A61B 17/0401* (2013.01); *A61B 2017/0409* (2013.01); *A61B 2017/0412* (2013.01); *A61B 2017/0414* (2013.01); *A61B 2017/0422* (2013.01); *A61B 2017/0425* (2013.01); *A61B 2017/0445* (2013.01); *A61B 2017/0446* (2013.01); *A61B 2017/0454* (2013.01); *A61B 2017/0458* (2013.01); *A61B 2017/0464* (2013.01)

(58) Field of Classification Search
CPC .......... A61B 17/0401; A61B 2017/044; A61B 2017/0445; A61B 2017/0409; A61B 2017/0435
See application file for complete search history.

(56) References Cited

U.S. PATENT DOCUMENTS 5,324,308 A 6/1994 Pierce
5,679,723 A 10/1997 Cooper
(Continued)

OTHER PUBLICATIONS

U.S. Appl. No. 13/791,072, filed Mar. 8, 2013, Knotless Suture Anchor and Method of Using Same
(Continued)

*Primary Examiner* — Tuan V Nguyen
(74) *Attorney, Agent, or Firm* — Schwegman Lundberg & Woessner, P.A.

(57) ABSTRACT

A suture anchor including a first portion and a second portion. The first portion defining a first suture bore and having an angled distal surface that extends in a plane oblique to a longitudinal axis of the suture anchor. The second portion defining a second suture bore and having an angled proximal surface that is complementary to the angled distal surface. The angled proximate surface extends in a plane oblique to the longitudinal axis. In a first configuration, the first portion and the second portion are aligned along the longitudinal axis, and the first suture bore is aligned with the second suture bore. In a second configuration, the first portion and the second portion are offset with respect to the longitudinal axis, and the first suture bore is offset from the second suture bore to retain a suture within the first suture bore and the second suture bore.

14 Claims, 5 Drawing Sheets

(56) References Cited

U.S. PATENT DOCUMENTS

| | | | |
|---|---|---|---|
| 6,520,980 B1* | 2/2003 | Foerster | A61B 17/0401 |
| | | | 606/232 |
| 7,674,276 B2 | 3/2010 | Stone et al. | |
| 7,713,285 B1 | 5/2010 | Stone et al. | |
| 7,976,565 B1 | 7/2011 | Meridew | |
| 8,512,405 B2 | 8/2013 | Baird | |
| 9,192,371 B2 | 11/2015 | Palese | |
| 2003/0009220 A1* | 1/2003 | Seyr | A61F 2/0811 |
| | | | 623/13.14 |
| 2006/0235413 A1 | 10/2006 | Denham et al. | |
| 2008/0097604 A1* | 4/2008 | Strobel | A61B 17/0401 |
| | | | 623/13.14 |
| 2008/0275469 A1 | 11/2008 | Fanton et al. | |
| 2011/0166599 A1 | 7/2011 | Jervis et al. | |
| 2014/0257355 A1 | 9/2014 | Palese | |
| 2014/0257381 A1 | 9/2014 | Palese | |

OTHER PUBLICATIONS

"U.S. Appl. No. 13/791,072, Examiner Interview Summary dated Dec. 26, 2014", 3 pgs.

"U.S. Appl. No. 13/791,072, Final Office Action dated Mar. 16, 2015", 10 pgs.

"U.S. Appl. No. 13/791,072, Non Final Office Action dated Oct. 16, 2014", 11 pgs.

"U.S. Appl. No. 13/791,072, Notice of Allowance dated Jul. 23, 2015", 8 pgs.

"U.S. Appl. No. 13/791,072, Response filed Jan. 16, 2015 to Non Final Office Action dated Oct. 16, 2014", 12 pgs.

"U.S. Appl. No. 13/791,072, Response filed Jul. 10, 2015 to Final Office Action dated Mar. 16, 2015", 9 pgs.

"U.S. Appl. No. 13/791,072, Response filed Sep. 2, 2014 to Restriction Requirement dated Jul. 3, 2014", 9 pgs.

"U.S. Appl. No. 13/791,072, Restriction Requirement dated Jul. 3, 2014", 9 pgs.

\* cited by examiner

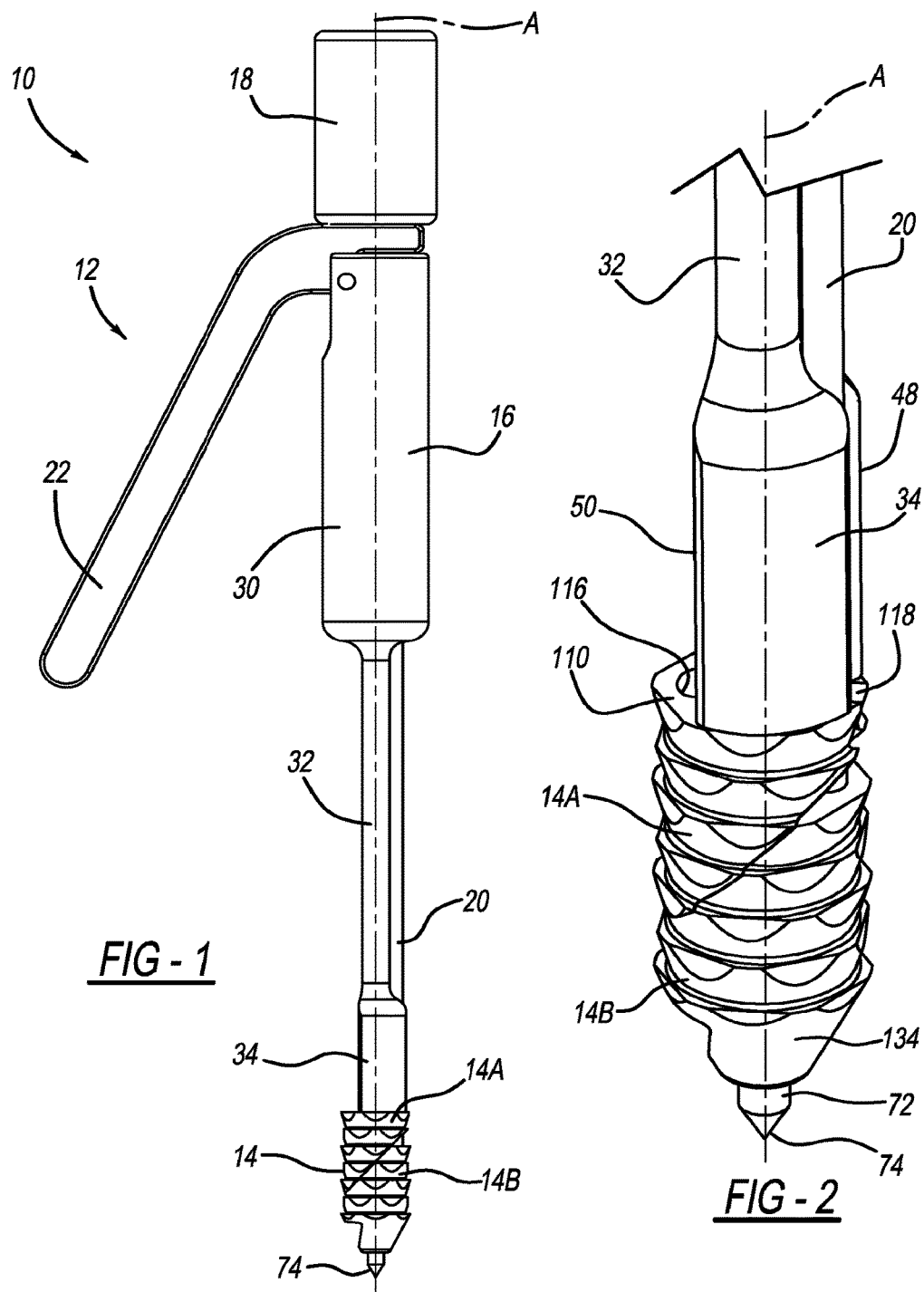

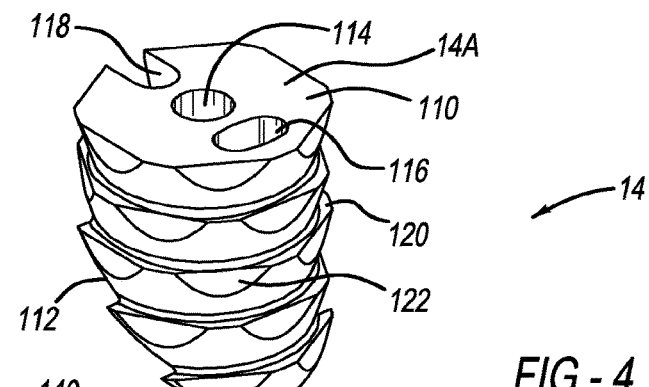
FIG - 4
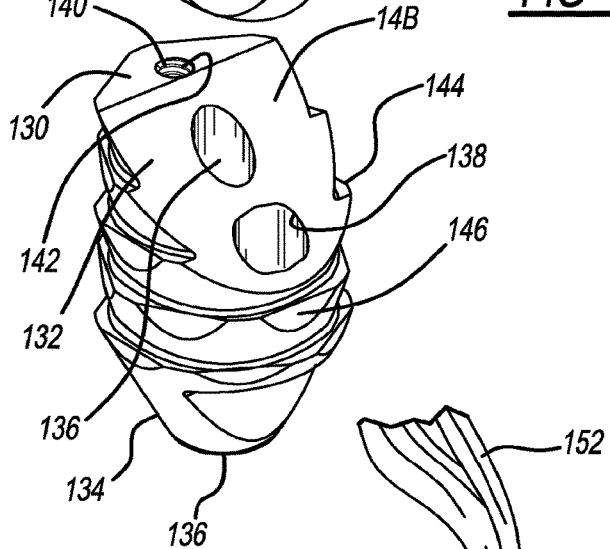
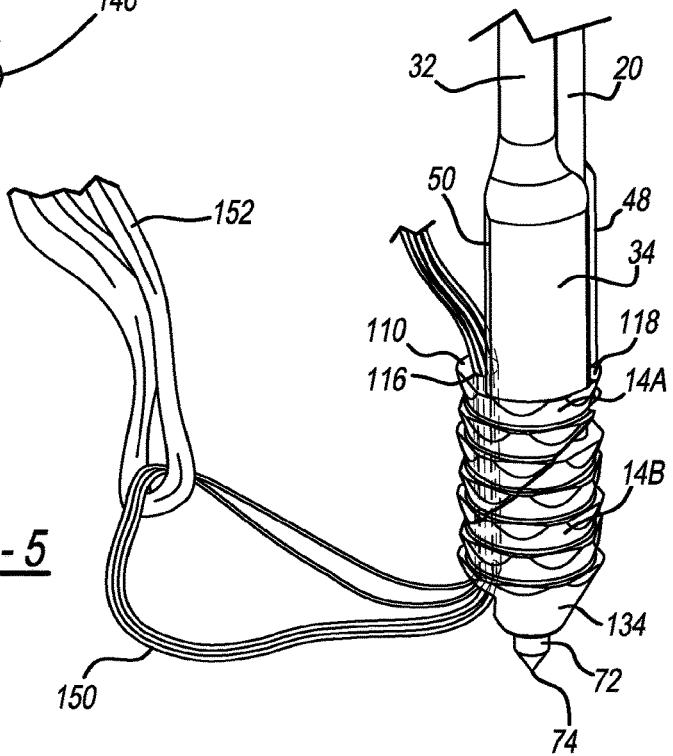
FIG - 5

KNOTLESS SUTURE ANCHOR AND METHOD OF USING SAME

FIELD

The present disclosure relates to a knotless suture anchor and a method of using the knotless suture anchor.

BACKGROUND

This section provides background information related to the present disclosure, which is not necessarily prior art.

Surgeons often use suture anchors to secure bone and tissue in place during a surgical procedure. A suture is connected to the anchor, which is typically implanted in bone. The suture is often connected to the anchor with a knot, which can be difficult to tie and makes tensioning cumbersome, particularly during surgery. The present teachings eliminate the need for connecting the suture to the anchor with a knot by providing a knotless suture anchor and method of using the same.

SUMMARY

This section provides a general summary of the disclosure, and is not a comprehensive disclosure of its full scope or all of its features.

The present teachings provide for a suture anchor including a first portion and a second portion. The first portion defining a first suture bore and having an angled distal surface that extends in a plane oblique to a longitudinal axis of the suture anchor. The second portion defining a second suture bore and having an angled proximal surface that is complementary to the angled distal surface. The angled proximate surface extends in a plane oblique to the longitudinal axis. In a first configuration, the first portion and the second portion are aligned along the longitudinal axis, and the first suture bore is aligned with the second suture bore. In a second configuration, the first portion and the second portion are offset with respect to the longitudinal axis, and the first suture bore is offset from the second suture bore to retain a suture within the first suture bore and the second suture bore.

The present teachings also provide for a system for knotlessly anchoring a suture. The system includes a cannula defining a center bore. A trocar is configured for receipt in the center bore. A deployment shaft is coupled to the cannula. A suture anchor is configured to be mounted to the trocar at a distal end of the cannula. The suture anchor includes a first anchor portion defining a first suture bore, and a second anchor portion defining a second suture bore. Actuation of the deployment shaft draws the second anchor portion against the first anchor portion and proximally toward the distal end of the cannula to misalign the first suture bore and the second suture bore to enable a suture to be secured in the first suture bore and the second suture bore.

The present teachings further provide for a method of knotlessly securing a suture to a suture anchor. The method includes implanting the suture anchor in a bone hole with an insertion tool, the suture anchor including a first portion defining a first suture bore and a second portion defining a second suture bore, the suture extending through the first and the second suture bores. The method further includes moving the second portion of the suture anchor relative to the first portion of the suture anchor using the insertion tool to misalign the first portion and the second portion, and to misalign the first and the second suture bores to retain the suture within the first and the second suture bores.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is a side view of a knotless suture anchor assembly according to the present teachings;

FIG. 2 is a close-up view of a distal portion the knotless suture anchor assembly of FIG. 1;

FIG. 4 illustrates a suture anchor according to the present teachings;

FIG. 5 illustrates a suture coupled to both the suture anchor and tissue;

Corresponding reference numerals indicate corresponding parts throughout the several views of the drawings.

DETAILED DESCRIPTION

Example embodiments will now be described more fully with reference to the accompanying drawings.

Figure 3:
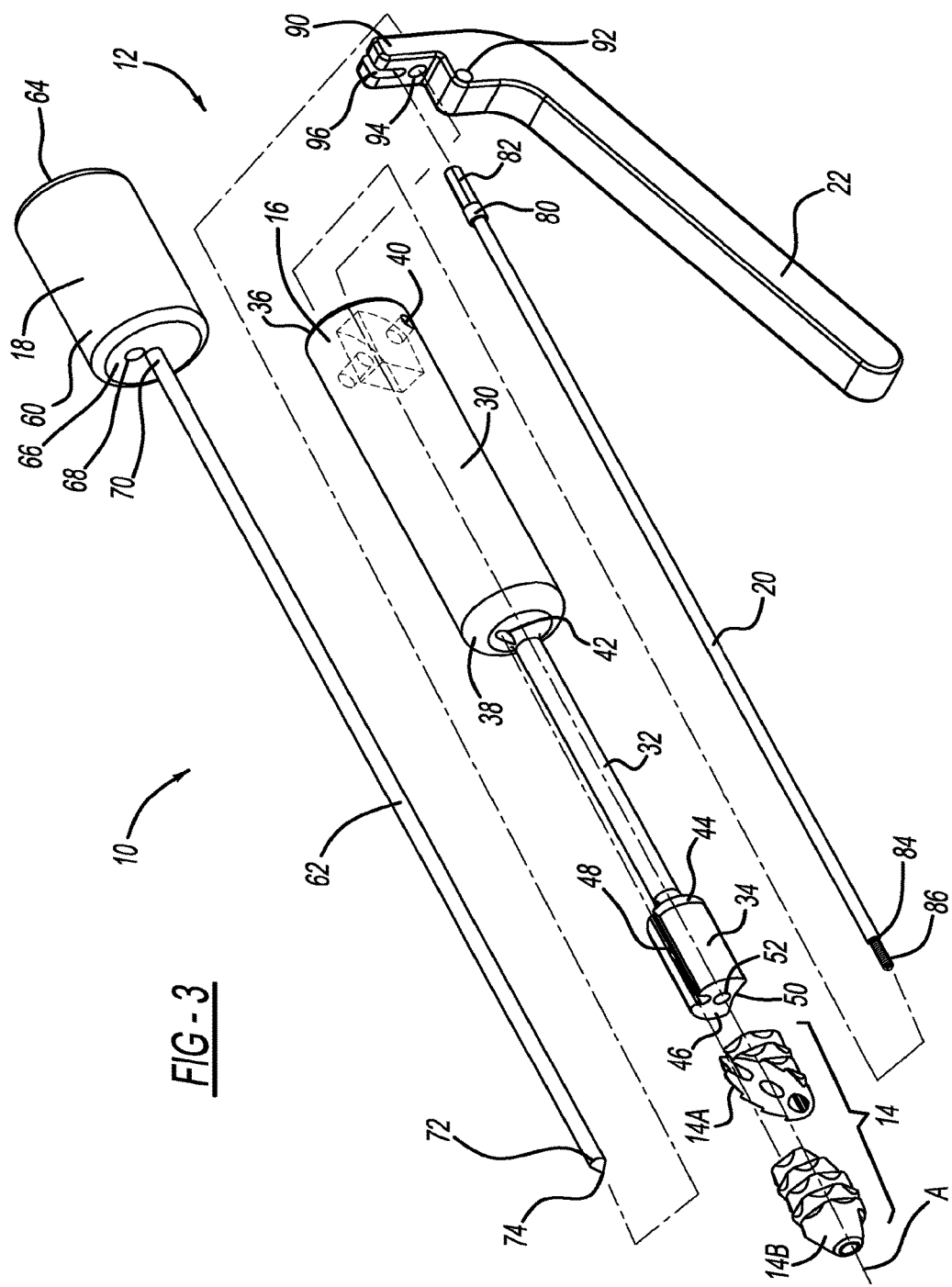
FIG. 3 is an exploded view of the knotless suture anchor assembly of FIG. 1.

With initial reference to FIGS. 1-3, a knotless suture anchor assembly according to the present teachings is generally illustrated at reference numeral 10. The assembly 10 generally includes an insertion tool 12 and a suture anchor 14. The insertion tool 12 includes a cannula 16, a trocar 18, a deployment shaft 20, and a handle 22.

The cannula 16 includes a proximal body 30, an elongated shaft 32, and a distal body 34. The proximal body 30 includes a proximal end 36 that is opposite to a distal end 38. Extending transverse through the proximal body 30 near the proximal end 36 is a bore 40, which is defined by the proximal body 30. The bore 40 extends generally perpendicular to, and offset from, a longitudinal axis A of the knotless suture anchor assembly 10 (FIGS. 1 and 2, for example). The proximal body 30 also defines a longitudinal bore 42 extending through the proximal body 30 between the proximal end 36 and the distal end 38. The longitudinal bore 42 extends generally parallel to, and spaced apart from, the longitudinal axis A.

The elongated shaft 32 extends from the distal end 38 of the proximal body 30 to a proximal end 44 of the distal body 34. The elongated shaft 32 has a diameter that is smaller than a diameter of the proximal body 30 and smaller than a diameter of the distal body 34.

The distal body 34 includes a distal end 46 that is opposite to the proximal end 44. The distal body 34 defines a channel 48 that extends across the distal body 34 generally between the proximal end 44 and the distal end 46. The channel 48 extends generally parallel to, and spaced apart from, the longitudinal axis A (FIGS. 1 and 2, for example).

The distal body 34 further includes a recessed portion 50 at a side of the distal body 34 generally opposite to the channel 48. The recessed portion 50 provides clearance for a suture 150 coupled to the suture anchor 14, as further described herein. The channel 48 provides a clearance for the deployment shaft 20, which extends through the channel 48 as described herein.

The distal end 46 of the distal body 34 is generally planar and extends in a plane that is generally perpendicular to the longitudinal axis A. The suture anchor 14 is arranged at the distal end 46 of the distal body 34 on the trocar 18, as explained further herein. The cannula 16 defines a center bore 52 that extends through the cannula 16 along the longitudinal axis A between the distal end 46 of the distal body 34 and the proximal end 36 of the proximal body 30.

The trocar 18 generally includes a trocar handle 60 and an elongated shaft 62. The trocar handle 60 includes a proximal end 64 and a distal end 66, which is opposite to the proximal end 64. The trocar handle 60 defines a bore 68, which extends between the proximal end 64 and the distal end 66 of the trocar handle 60. The bore 68 need not extend entirely to the proximal end 64, and thus may terminate prior to reaching the proximal end 64 to form a blind bore. The bore 68 is sized and positioned to accommodate the deployment shaft 20 as further described herein.

The elongated shaft 62 includes a proximal end 70 and a distal end 72, which is opposite to the proximal end 70. The proximal end 70 is connected to the distal end 66 of the trocar handle 60. At the distal end 72 of the elongated shaft 62 is a pointed tip 74. The elongated shaft 62 is generally rigid and the pointed tip 74 is configured to permit the trocar 18 to pierce bone and form a bone hole as further described herein.

The deployment shaft 20 includes a proximal end 80 and a coupling member 82 at the proximal end 80. The coupling member 82 can be any suitable coupling member to couple the deployment shaft 20 to the handle 22, such as a surface configured to be rigidly secured in the channel. The deployment shaft 20 further includes a distal end 84, which is opposite to the proximal end 80. At the distal end 84 is a threaded portion 86, which can engage the suture anchor 14 to connect the deployment shaft 20 to the suture anchor 14, as described further herein. The deployment shaft 20 is generally rigid, and can be made of any suitable rigid material, such as a rigid metal or polymer.

The handle 22 includes a flange 90. The flange 90 defines a first bore 92, a second bore 94 orthogonal to the first bore 92, and a channel 96 parallel to the second bore 94. The handle 22 is pivotally coupled to the proximal body 30 with a suitable fastener extending through both the first bore 92 of the flange 90 and the bore 40 of the proximal body 30 of the cannula 16. The handle 22 is arranged such that the second bore 94 is aligned with the center bore 52 of the cannula 16 and the channel 96 is aligned with the longitudinal bore 42 of the cannula 16.

As assembled, the elongated shaft 62 of the trocar 18 extends through both the second bore 94 of the handle 22 and the center bore 52 of the cannula 16. The flange 90 of the handle 22 is between the trocar handle 60 and the proximal end 36 of the cannula 16. Thus, the distal end 66 of the trocar handle 60 is seated on the flange 90 of the handle 22. The distal end 72 of the elongated shaft 62 extends out from within the center bore 52 beyond the distal end 46 of the distal body 34. The suture anchor 14 is seated on the distal end 72 of the elongated shaft 62, and the pointed tip 74 of the elongated shaft 62 extends out from within the suture anchor 14.

The deployment shaft 20 is connected to the handle 22 through cooperation between the coupling member 82 of the deployment shaft 20 and the channel 96 of the flange 90. When the trocar handle 60 is seated on the flange 90 of the handle 22, the bore 68 of the trocar handle 60 accommodates the coupling member 82, which extends beyond the flange 90 of the handle 22. The deployment shaft 20 extends through the longitudinal bore 42 of the cannula 16, and further extends to and through the channel 48 of the distal body 34. The threaded portion 86 at the distal end 84 of the deployment shaft 20 couples with the suture anchor 14 to retain the suture anchor 14 on the distal end 72 of the trocar 18, as further described herein.

With additional reference to FIG. 4, specific features of the suture anchor 14 will now be described. The suture anchor 14 generally includes a first portion 14A and a second portion 14B. The first portion 14A generally includes a proximal surface 110 and a distal surface 112, which is opposite to the proximal surface 110. The proximal surface 110 is generally planar and extends in a plane generally perpendicular to the longitudinal axis A when the suture anchor 14 is seated on the elongated shaft 62 of the trocar 18. The distal surface 112 is angled with respect to the proximal surface 110 and extends in a plane that is angled and not perpendicular to, or oblique to, the longitudinal axis A when the first portion 14A is seated on the trocar 18.

The first portion 14A defines a center bore 114, a suture bore 116, and a deployment shaft recess or bore 118. The center bore 114 extends between the proximal surface 110 and the distal surface 112 along the longitudinal axis A when the first portion 14A is coupled to the trocar 18. The suture bore 116 also extends between the proximal surface 110 and the distal surface 112. When the first portion 14A is seated on the trocar 18, the suture bore 116 is aligned with the recessed portion 50 of the distal body 34 of the cannula 16, as illustrated in FIG. 3. The suture bore 116 is thus arranged such that it extends generally parallel to a longitudinal axis A and spaced apart from the longitudinal axis A. The deployment shaft recess 118 can be a cutout in the first portion 14A as illustrated, or a bore extending through the first portion 14A. The deployment shaft recess 118 extends between the proximal surface 110 and the distal surface 112. The deployment shaft recess 118 is configured to receive the distal end 84 of the deployment shaft 20. When the first portion 14A is coupled to the cannula 16, the first portion 14A is arranged such that the deployment shaft recess 118 is aligned with the channel 48 of the distal body 34. The deployment shaft recess 118 extends generally parallel to and spaced apart from the longitudinal axis A. The center bore 114 is thus arranged between the suture bore 116 and the deployment shaft recess 118, and is configured to receive the elongated shaft 62 of the trocar 18.

Extending from a periphery of the first portion 14A between the proximal surface 110 and the distal surface 112 are a plurality of retention ribs 120. The retention ribs 120 are generally circular and extend generally radially from the first portion 14A. Also extending from the periphery of the first portion 14A are a plurality of retention teeth 122. The retention teeth 122 are generally spaced apart along the retention ribs 120. The retention ribs 120 and the retention teeth 122 are configured to engage an inner wall of a bone hole to retain the first portion 14A within the bone hole as further described herein. The retention ribs 120 and the retention teeth 122 can be any suitable retention members suitable for retaining the first portion 14A within a bone hole.

With continued reference to FIG. 4, the second portion 14B of the suture anchor 14 generally includes a first proximal surface 130, a second proximal surface 132, and a distal cone-shaped surface 134. The first proximal surface 130 is adjacent to the second proximal surface 132. The first proximal surface 130 is generally planar and extends in a plane that is generally perpendicular to the longitudinal axis A when the second portion 14B is seated on the trocar 18. The second proximal surface 132 is angled with respect to the first proximal surface 130. The second proximal surface 132 thus extends in a plane that is not perpendicular to, or oblique to, the longitudinal axis A when the second portion 14B is seated on the trocar 18.

The second portion 14B defines a center bore 136, a suture bore 138, and a deployment shaft bore 140. The center bore 136 extends between the second proximal surface 132 and the distal cone-shaped surface 134. The center bore 136 extends along the longitudinal axis A when the second portion 14B is seated on the trocar 18, and thus the center bore 136 of the second portion 14B is aligned with a center bore 114 of the first portion 14A. The longitudinal axis A is also a longitudinal axis of the suture anchor 14. A suture bore 138 extends from the second proximal surface 132 to the distal cone-shaped surface 134. The suture bore 138 extends generally parallel to the longitudinal axis A, but spaced apart therefrom, when the second portion 14B is seated on the trocar 18. The suture bore 138 of the second portion 14B is aligned with the suture bore 116 of the first portion 14A prior to deployment of the suture anchor 14, as described in further detail herein.

The deployment shaft bore 140 extends from the first proximal surface 130 towards the distal cone-shaped surface 134. The deployment shaft bore 140 may extend to the distal cone-shaped surface 134, or may terminate prior to reaching the distal cone-shaped surface 134. The deployment shaft bore 140 may define threads 142 therein. The threads 142 extend from the first proximal surface 130 to any suitable distance within the deployment shaft bore 140 to permit coupling with the threaded portion 86 of the deployment shaft 20. Extending from an outer diameter of the second portion 14B are a plurality of annular retention ribs 144 and a plurality of retention teeth 146. The retention ribs 144 are generally similar to the retention ribs 120 of the first portion 14A, and the retention teeth 146 are generally similar to the retention teeth 122 of the first portion 14A. The suture anchor 14 can be made of any suitable biocompatible material. For example, the suture anchor 14 can be made of a suitable polymer, such as PEEK, or a suitable metallic.

Coupling of the suture anchor 14 with the insertion tool 12 will now be described in additional detail. The first portion 14A of the suture anchor 14 is arranged such that the proximal surface 110 abuts the distal end 46 of the distal body 34, which is part of the cannula 16. The center bore 114 is aligned with the center bore 52 of the cannula 16 and the distal end 72 of the trocar 18 extends through the center bore 114. The deployment shaft recess 118 is aligned with the channel 48 of the cannula 16, and the suture bore 116 is aligned with the recessed portion 50 of the cannula 16.

The second portion 14B of the suture anchor 14 abuts the first portion 14A. Specifically, the second proximal surface 132 of the second portion 14B abuts the distal surface 112 of the first portion 14A. The distal end 72 of the trocar 18 extends through the center bore 136 of the second portion 14B, which is aligned with the center bore 114 of the first portion 14A. The suture bore 138 of the second portion 14B is aligned with the suture bore 116 of the first portion 14A. The deployment shaft bore 140 is aligned with the deployment shaft recess 118 of the first portion 14A.

The deployment shaft 20 extends through the deployment shaft recess 118 of the first portion 14A, and into the deployment shaft bore 140 of the second portion 14B. The threaded portion 86 of the deployment shaft 20 threadably engages the threads 142 of the deployment shaft bore 140 to retain the second portion 14B on the trocar 18. The first portion 14A is thus retained between the second portion 14B and the cannula 16. Although the deployment shaft 20 is illustrated as being retained within the deployment shaft bore 140 with a threaded coupling, the deployment shaft 20 may be retained within the deployment shaft bore 140 in any suitable manner using any suitable coupling, such as a press fit or an overmold.

With additional reference to FIGS. 5-7, a method of using the knotless suture anchor assembly 10 to anchor suture 150 in bone 210 will now be described. Although the suture 150 is described as securing tissue 152 to bone 210, the suture 150 can be used to secure any suitable tissue or bone at any suitable location. The suture 150 can be coupled to the tissue 152 prior to or after the suture anchor 14 is implanted in the bone 210. Prior to implanting the suture anchor 14 in the bone 210, the suture 150 is passed through the suture bore 116 and the suture bore 138 of the suture anchor 14. The suture anchor 14 is then implanted in the bone 210 using the insertion tool 12.

Figure 6:
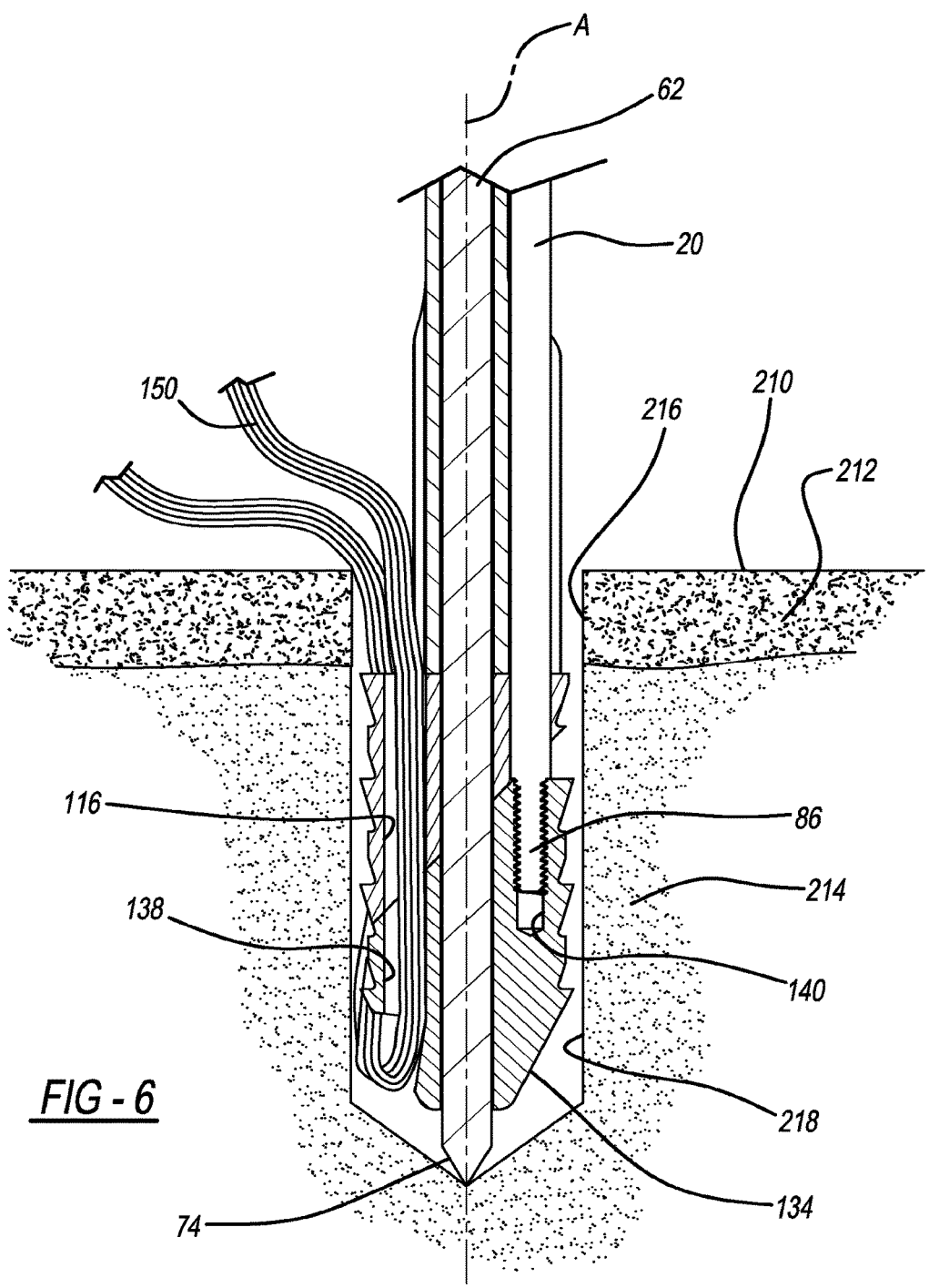
FIG. 6 illustrates the suture anchor with a suture coupled thereto arranged in a bone hole prior to deployment of the suture anchor.

As illustrated in FIG. 6 for example, the suture anchor 14 is implanted in a bone hole 216 extending through cortical bone 212 and into cancellous bone 214. The bone hole 216 may be pre-formed with a suitable drill or punch for example, or the insertion tool 12 may be impacted into the bone 210 to form the bone hole 216. For example, the insertion tool 12 may be arranged such that the pointed tip 74 is at the surface of the cortical bone 212 and then the proximal end 64 of the trocar handle 60 may be impacted, such as with a suitable impactor, in order to drive the suture anchor 14 into the bone 210 and form the bone hole 216.

Figure 7:
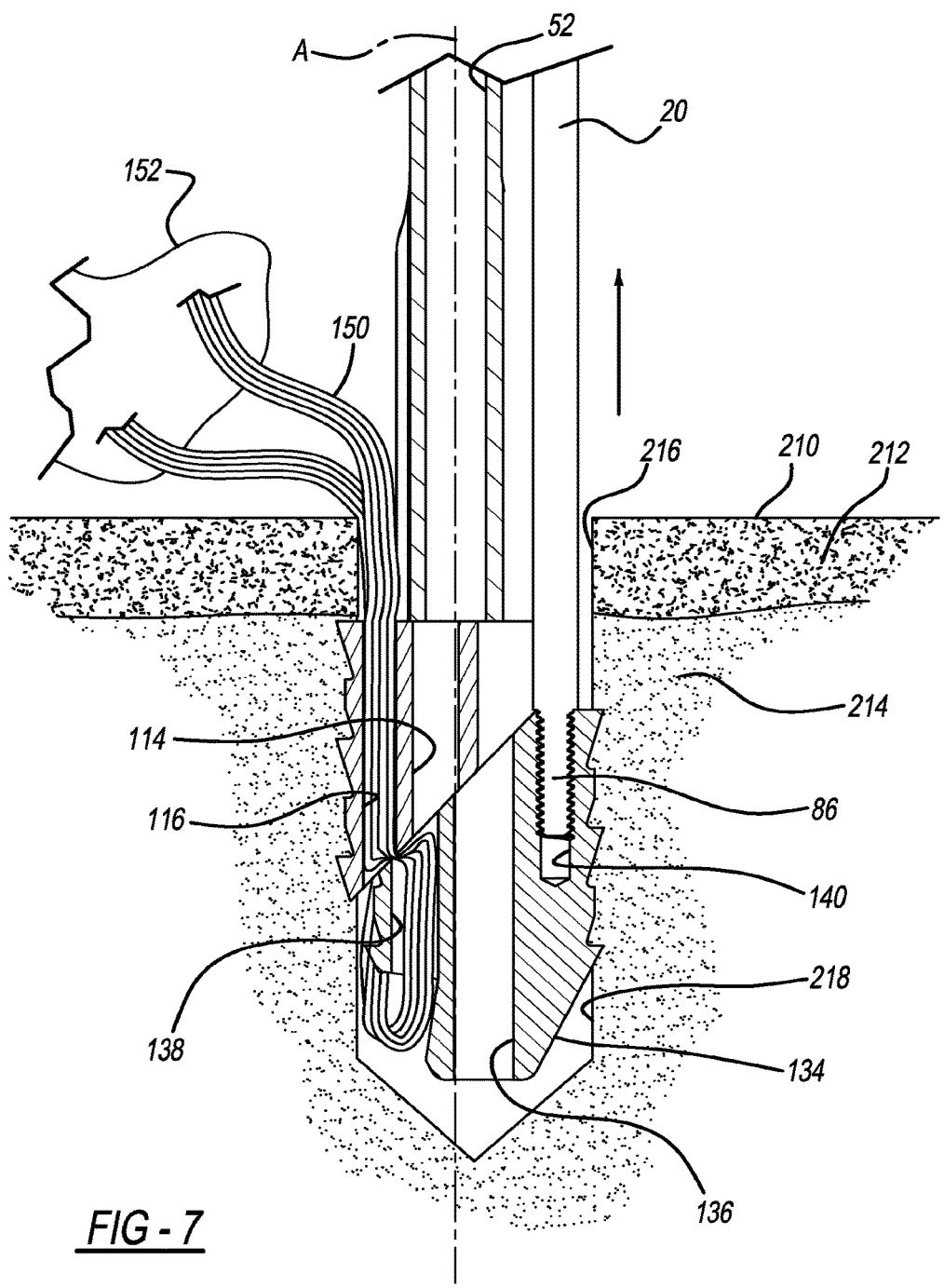
FIG. 7 illustrates the suture anchor deployed in the bone hole to secure the suture to the suture anchor and retain tissue against bone.

With additional reference to FIG. 7, after the suture anchor 14 is seated in the bone hole 216, the trocar 18 is removed from cooperation with the remainder of the insertion tool 12. To deploy the suture anchor 14 and thus retain the suture anchor 14 within the bone hole 216, the handle 22 is depressed, which pulls the distal end 84 of the deployment shaft 20 proximally toward and into the distal body 34 of the cannula 16. Because the deployment shaft 20 is coupled to the second portion 14B of the suture anchor 14, the deployment shaft 20 will pull the second portion 14B proximally toward the cannula 16 and press the second proximal surface 132 of the second portion 14B against the distal surface 112 of the first portion 14A. This movement will force each of the first portion 14A and the second portion 14B radially away from the longitudinal axis A in opposite directions and into engagement with the bone 214 of the inner wall 218 defining the bone hole 216. This movement will also misalign the center bore 114 and the center bore 136 of the first portion 14A and the second portion 14B respectively.

The suture bore 116 and the suture bore 138 of the first portion 14A and the second portion 14B respectively will also become misaligned, which will pinch the suture 150 between the suture bore 116 and the suture bore 138, and thus retain the suture 150 within the suture bores 116 and 138. In this manner, the suture 150 will be coupled to the suture anchor 14 without the need for a knot. Continued actuation of the handle 22 will cause the threaded portion 86 of the deployment shaft 20 to disengage the threads 142 of the deployment shaft bore 140, such as by stripping or pulling out through the threads 142. This continued actuation of the handle 22 will further force the first and second portions 14A and 14B of the suture anchor 14 away from the longitudinal axis A and into the inner wall 218 of the bone hole 216, thereby retaining the suture anchor 14 within the bone hole 216. The tissue 152 coupled to the suture 150 will thus be retained against the bone 210 with the anchored suture 150.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A suture anchor comprising:
a first portion defining a first suture bore and having an angled distal surface that extends in a plane oblique to a longitudinal axis of the suture anchor;
a second portion defining a second suture bore and having an angled proximal surface that is complementary to the angled distal surface of the first portion, the angled proximate surface extends in a plane oblique to the longitudinal axis;
wherein in a first configuration, the first portion and the second portion are aligned along the longitudinal axis of the suture anchor, and the first suture bore is aligned with the second suture bore; and
wherein in a second configuration, the first portion and the second portion are offset with respect to the longitudinal axis, and the first suture bore is offset from the second suture bore to pinch a suture within the first suture bore and the second suture bore to retain and restrict movement of the suture to within the first suture bore and the second suture bore.

2. The suture anchor of claim 1, wherein the first portion defines a first deployment shaft bore and the second portion defines a second deployment shaft bore; and
wherein pulling the second portion towards the first portion with a deployment shaft extending through the first deployment shaft bore and engaging the second deployment shaft bore moves the suture anchor to the second configuration.

3. The suture anchor of claim 1, wherein the first portion defines a first center bore and the second portion defines a second center bore, both the first center bore and the second center bore are configured to receive a shaft to retain the suture anchor in the first configuration.

4. The suture anchor of claim 1, wherein the first portion and the second portion define a plurality of retention teeth arranged about a perimeter thereof.

5. The suture anchor of claim 1, wherein the second portion further defines a conical, distal portion.

6. The suture anchor of claim 1, wherein the first portion defines a proximal planar surface that extends in a plane generally perpendicular to the longitudinal axis.

7. A system for knotlessly anchoring a suture comprising:
a cannula defining a center bore;
a trocar configured for receipt in the center bore;
a deployment shaft coupled to the cannula; and
a suture anchor configured to be mounted to the trocar at a distal end of the cannula, the suture anchor including:
a first anchor portion defining a first suture bore; and
a second anchor portion defining a second suture bore;
wherein the first anchor portion includes a first angled surface and the second anchor portion includes a second angled surface that is in contact with the first angled surface, the first and second angled surfaces extend oblique to a longitudinal axis of the suture anchor;
wherein actuation of the deployment shaft draws the second anchor portion against the first anchor portion and proximally toward the distal end of the cannula to misalign the first suture bore and the second suture bore to enable a suture to be secured in the first suture bore and the second suture bore.

8. The system of claim 7, wherein the first anchor portion defines a first center bore and the second anchor portion defines a second center bore, the trocar configured to extend through the first center bore and the second center bore, wherein the trocar is withdrawn from the first and second center bores upon actuation of the deployment shaft.

9. The system of claim 7, wherein the deployment shaft is configured to removably couple with the second anchor portion to pull the second anchor portion proximally toward the cannula upon actuation of a handle in cooperation with the deployment shaft.

10. The system of claim 7, wherein the deployment shaft is coupled to a handle of the cannula such that actuation of the handle moves the deployment shaft and the second anchor portion coupled to the deployment shaft.

11. The system of claim 7, wherein the deployment shaft engages the second anchor portion prior to actuation of the deployment shaft.

12. A suture anchor comprising:
a first portion defining a first suture bore, a first deployment shaft bore, and a first center bore, the first portion having an angled distal surface that extends in a plane oblique to a longitudinal axis of the suture anchor;
a second portion extending from a proximal end to a distal end, the second portion defining a second suture bore, a second deployment shaft bore, and a second center bore, the second portion having a proximal surface and an angled surface, the proximal surface including the deployment shaft bore and the angled surface positioned between the proximal surface and the distal end and including the second suture bore and the second center bore, wherein the angled surface is complementary to the angled distal surface of the first portion, and wherein the angled surface extends in a plane oblique to the longitudinal axis;
wherein in a first configuration, the first portion and the second portion are aligned along the longitudinal axis of the suture anchor, and the first suture bore is aligned with the second suture bore; and
wherein in a second configuration, the first portion and the second portion are offset with respect to the longitudinal axis, and the first suture bore is offset from the second suture bore to retain a suture within the first suture bore and the second suture bore.

13. The suture anchor of claim 12, wherein the proximal surface is perpendicular to the longitudinal axis.

14. The suture anchor of claim 13, wherein the first deployment shaft bore is a recess that is open to a side surface of the first portion.

* * * * *